United States Patent [19]

Mrozik

[11] Patent Number: 4,866,060

[45] Date of Patent: Sep. 12, 1989

[54] USE OF THE NATURAL PRODUCT MARCFORTINES AS ANTIPARASITIC AGENTS

[75] Inventor: Helmut Mrozik, Matawan, N.J.

[73] Assignee: Merck & Co., Inc., Rahway, N.J.

[21] Appl. No.: 233,785

[22] Filed: Aug. 19, 1988

[51] Int. Cl.$^4$ .................... A61K 31/50; A61K 31/495
[52] U.S. Cl. ................................................. 514/250
[58] Field of Search ........................................ 514/250

[56] References Cited

PUBLICATIONS

Chemical Abstracts 93:239750b (1980).
Chemical Abstracts 95:133215g (1981).
Polonsky et al, *Journal of the Chemical Society Chemical Communications* 1980 pp. 601–602.
Prange et al, *Tetrahedron Letters* 22 pp. 1977–1980 (1981).
Yamazaki et al, Tetrahedron Letters 22 pp. 135–136 (1981).

*Primary Examiner*—Jerome D. Goldberg
*Attorney, Agent, or Firm*—David L. Rose; Hesna J. Pfeiffer

[57] ABSTRACT

The marcfortines (marcfortines A, B, and C) are known fungal metabolites isolated from the known fungus *Penicillium roqueforti*. The compounds are useful antiparasitic agents for the treatment of diseases caused by endo and ecto parasites. Antiparasitic compositions which contain one or more of the marcfortines as the active ingredient are disclosed.

14 Claims, No Drawings

USE OF THE NATURAL PRODUCT MARCFORTINES AS ANTIPARASITIC AGENTS

BACKGROUND OF THE INVENTION

The marcfortines are known compounds and are disclosed by Polonsky et al in *Journal of the Chemical Society Chemical Communications* 1980 601–602 (Marcfortine A) and *Tetrahedron Letters* 1981 22 1977–1980 (Marcfortines B and C). The compounds are fungal metabolites of *Penicillium roqueforti.* No uses for the compounds are suqqested. The marcfortines are structurally related to paraherquamide and dihydroparaherquamide which are also known compounds. Paraherquamide and dihydroparaherquamide are disclosed in Yamazaki et al in *Tetrahedron Letters* 1981 22 135 136. Paraherquamide is a fungal metabolite of *Penicillium paraherquei.* Dihydroparaherquamide is prepared from paraherquamide by catalytic hydrogenation. No uses for the compounds are suggested.

SUMMARY OF THE INVENTION

This invention is concerned with the use of marcfortines A, B, and C as antiparasitic agents. Thus it is an object of this invention to describe the use of these compounds as antiparasitic agents. A further object is to describe compositions which contain the marcfortines as the active ingredient thereof. Further objects will become apparent from a reading of the following description.

DESCRIPTION OF THE INVENTION

Marcfortine A has the following structure:

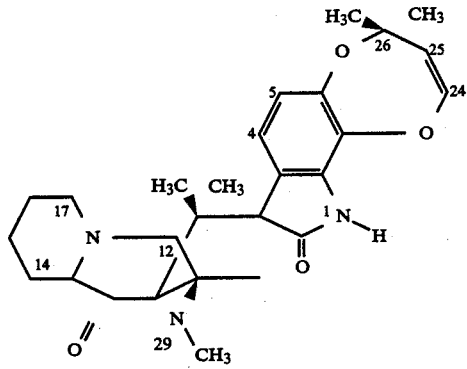

Marcfortine B has the following structure:

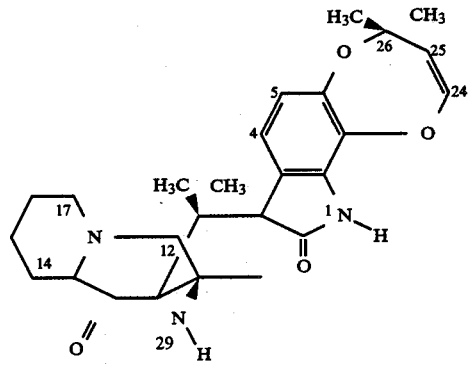

Marcfortine C has the following structure:

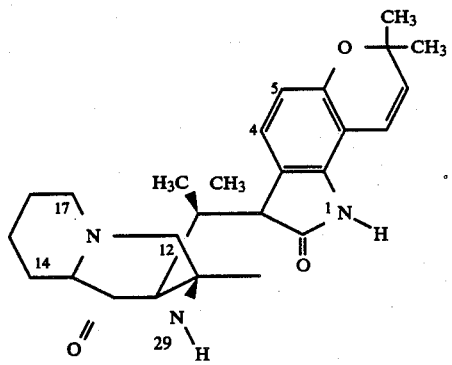

Marcfortines A, B and C are isolated as fungal metabolites of *Penicillium roqueforti,* along with the previously known roquefortine, using standard fermentation and isolation techniques. The isolation, as well as the analytical and structural characteristics of marcfortine A, are described in detail in Polonsky et al *Journal of the Chemical Society Chemical Communications* 1980 601–602. The isolation, as well as the analytical and structural characteristics of marcfortines B and C, are described in detail in Polonsky et al *Tetrahedron Letters* 1981 22 1977–1980.

From the extraction of 196 g of a lyophilized mycelium of the fermentation of *Penicillium roqueforti,* an alkaloidal extract of 380 mg is produced. Chromatography yields 24 mg of roquefortine, 79 mg of marcfortine A and marcfortines B and C.

The marcfortines are unexpectedly potent antiparastic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertaqia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition are also active against Dirofilaria in dogs, Nematospiroides and Syphacia in rodents, biting insects, and migrating diperous larvae such as Hypoderma sp. in cattle, and Gastrophilus in horses.

The instant compounds are also useful against endo and ecto parasites which cause parasitic diseases in humans. Examples of such endoparasites which infect man include gastro intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra-intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans. The instant compounds when administered orally or parenterally are administered at a dosage rate of from 0.05 to 20 mg/kg of animal body weight.

The instant compounds are also useful against common household pests such as Blatella sp. (cockroach), Tineola sp. (clothes moth), Attagenus sp. (carpet beetle), *Musca domestica* (housefly), and against *Solenopsis Invicta* (imported fire ant).

The compounds are furthermore useful against agricultural pests such as aphids (Acyrthiosiphon sp.), locusts, and boll weevils as well as against insect pests which attack stored grains such as Tribolium sp. and against immature stages of insects living on plant tissue. The compounds are also useful as a nematocide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, bolus, or drench form or alternatively they can be mixed in the animals feed. The capsules, tablets, boluses and drenches are comprised of the active ingredient in combination with an appropriate carrier vehicle such as starch, talc, magnesium stearate, or di-calcium phosphate. These unit dosage forms are prepared by intimately mixing the active ingredient with suitable finely-powdered or liquid inert ingredients including diluents, fillers, disintegrating agents, suspending agents, and/or binders such that a uniform mixture, solution or suspension is obtained. The unit dosage form preferably will contain from 0.005 to 10% by weight of the active ingredient. An inert ingredient is one that will not react with the instant compounds and which is non-toxic to the animal being treated. Suitable inert ingredients include starch, lacrose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5.0% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.5 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 0.005 to 15 mg per kg of animal body weight, either in a single dose or in several doses spaced a few days apart, generally gives good results. A single dose of one of the instant compounds normally gives excellent control however repeat doses may be given to combat re infection or for parasite species which are unusually persistent. The techniques for administering these compounds to animals are known to those skilled in the veterinary field.

The compounds of this invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

What is claimed is:

1. A method for the prevention or treatment of helminth and arthropod infections in an animal which comprises administering to said animal an antiparasitically effective amount of marcfortine A, marcfortine B or marcfortine C.

2. The method of claim 1 wherein the active ingredient is marcfortine A.

3. The method of claim 1 wherein the active ingredient is marcfortine B.

4. The method of claim 1 wherein the active ingredient is marcfortine C.

5. The method of claim 1 wherein the active ingredient is administered orally to animals at a dose of from 0.05 to 20 mg per kg of animal body weight.

6. The method of claim 1 wherein the active ingredient is administered to animals parenterally by injection of a suitable liquid formulation at a dose of from 0.05 to 20 mg of active ingredient per kg of body weight.

7. A feed composition useful for the prevention and treatment of helminth and arthropod infections which comprises from 0.001 to 5% by weight of marcfortine A or marcfortine B or marcfortine C as the active ingredient and feedstuff ingredients.

8. The composition of claim 7 wherein the active ingredient is marcfortine A.

9. The composition of claim 7 wherein the active ingredient is marcfortine B.

10. The composition of claim 7 wherein the active ingredient is marcfortine C.

11. A tablet composition useful for the prevention and treatment of helminth and arthropod infections which comprises from 0.005 to 10% by weight of marcfortine A, marcfortine B or marcfortine C as the active ingredient and one or more inert ingredients.

12. The composition of claim 11 wherein the active ingredient is marcfortine A.

13. The composition of claim 11 wherein the active ingredient in marcfortine B.

14. The composition of claim 11 wherein the active ingredient is marcfortine C.

* * * * *

UNITED STATES PATENT AND TRADEMARK OFFICE
CERTIFICATE OF CORRECTION

PATENT NO. : 4,866,060

DATED : September 12, 1989

INVENTOR(S) : H. Mrozik

Page 1 of 2

It is certified that error appears in the above-identified patent and that said Letters Patent is hereby corrected as shown below:

Delete the structure in column 1, lines 35-50 and insert therefor the following:

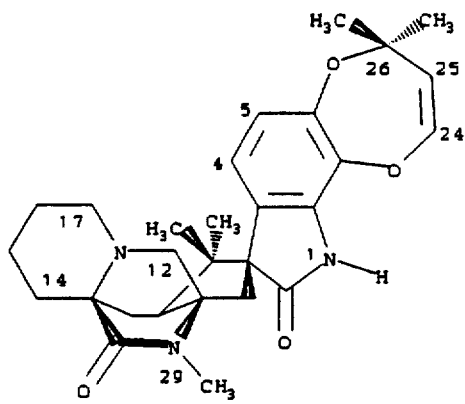

Delete the structure in column 1, lines 52-69 and insert therefor the following:

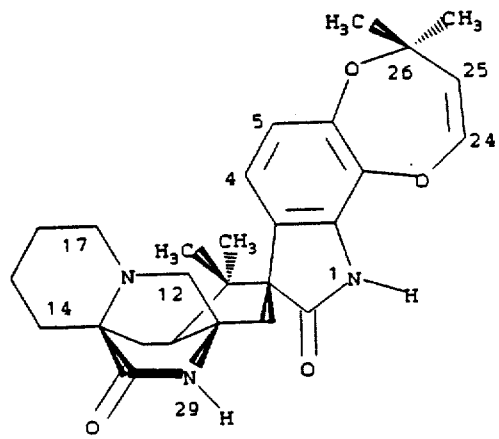

UNITED STATES PATENT AND TRADEMARK OFFICE
CERTIFICATE OF CORRECTION

PATENT NO. : 4,866,060
DATED : September 12, 1989
INVENTOR(S) : H. Mrozik

It is certified that error appears in the above-identified patent and that said Letters Patent is hereby corrected as shown below:

Delete the structure in Column 2 lines 2-17 and insert therefor the following:

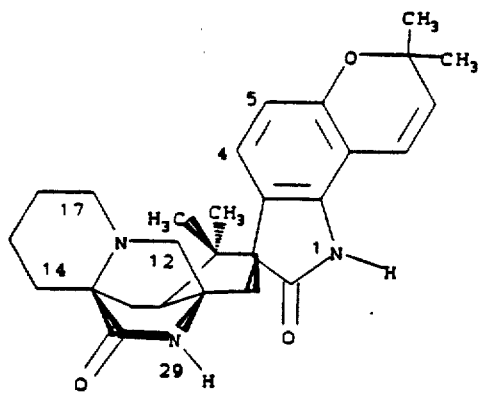

Signed and Sealed this

Eleventh Day of September, 1990

Attest:

HARRY F. MANBECK, JR.

*Attesting Officer*   *Commissioner of Patents and Trademarks*